United States Patent
Gavrish et al.

(10) Patent No.: US 9,249,382 B2
(45) Date of Patent: Feb. 2, 2016

(54) DEVICES AND METHODS FOR THE SELECTIVE ISOLATION OF MICROORGANISMS

(75) Inventors: Ekaterina Gavrish, Boston, MA (US); Kim Lewis, Newton, MA (US); Slava S. Epstein, Dedham, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 1350 days.

(21) Appl. No.: 11/732,346

(22) Filed: Apr. 3, 2007

(65) Prior Publication Data

US 2007/0275451 A1 Nov. 29, 2007

Related U.S. Application Data

(60) Continuation-in-part of application No. 10/993,454, filed on Nov. 18, 2004, now abandoned, which is a division of application No. 10/143,551, filed on May 10, 2002, now Pat. No. 7,011,957, which is a continuation-in-part of application No. 10/135,960, filed on May 1, 2002, now abandoned.

(60) Provisional application No. 60/325,052, filed on Sep. 26, 2001, provisional application No. 60/789,101, filed on Apr. 4, 2006.

(51) Int. Cl.
  *C12M 1/00* (2006.01)
  *C12M 1/12* (2006.01)
  *C12M 1/26* (2006.01)
  *C12M 1/16* (2006.01)

(52) U.S. Cl.
  CPC ............... *C12M 23/20* (2013.01); *C12M 25/14* (2013.01); *C12M 29/04* (2013.01); *C12M 33/14* (2013.01); *C12M 47/02* (2013.01); *C12M 1/16* (2013.01)

(58) Field of Classification Search
  CPC ................................ C12M 33/14; C12M 1/16
  USPC ............................................ 435/309.1, 297.1
  See application file for complete search history.

(56) References Cited

U.S. PATENT DOCUMENTS

| | | | | |
|---|---|---|---|---|
| 3,301,769 | A * | 1/1967 | Robert Steel | 435/34 |
| 4,917,793 | A * | 4/1990 | Pitt et al. | 210/94 |
| 5,079,168 | A * | 1/1992 | Amiot | 435/297.2 |
| 5,081,035 | A | 1/1992 | Halberstadt et al. | |
| 5,104,804 | A * | 4/1992 | Humphries et al. | 435/287.1 |
| 5,409,829 | A * | 4/1995 | Mussi et al. | 435/396 |
| 6,040,153 | A * | 3/2000 | Lemonnier | 435/30 |
| 6,284,531 | B1 * | 9/2001 | Zhu et al. | 435/305.3 |

(Continued)

OTHER PUBLICATIONS

McFeters et al., "Survival of Coliform Bacteria in Natural Waters: Field and Laboratory Studies with Membrane-Filter Chambers", 1972 Applied Microbiology, vol. 24 No. 5, p. 805-811.*

(Continued)

*Primary Examiner* — Jonathan Hurst
(74) *Attorney, Agent, or Firm* — Ann-Louise Kerner; DLA Piper LLP (US)

(57) ABSTRACT

Devices and methods for isolating and/or culturing microorganisms are provided. The devices comprise one or more semi-permeable membranes and may additionally include a growth medium for the microorganism. The devices and methods described herein can be used to isolate and culture both known and novel microorganisms from any environment.

20 Claims, 6 Drawing Sheets

(56) References Cited

U.S. PATENT DOCUMENTS

2003/0059866 A1 3/2003 Lewis et al.
2003/0091989 A1* 5/2003 Davis et al. .................. 435/5

OTHER PUBLICATIONS

Curtis, et al., "Estimating Prokaryotic Diversity and its Limits", Proc. Nat. Acad. Sci. USA, 99:10494-10499 (2002).
Delong, "Microbial Seacapes Revisited", Curr. Opin. Microbiol., 4:290-295 (2001).
Dojka, et al., "Expanding the Known Diversity and Environmental Distribution of an Uncultured Phylogenetic Division of Bacteria", Appl. Environ. Microbiol, 66:1617-1621 (2000).
Giovannoni, et al., "Genetic Diversity in Sargasso Sea Bacterioplankton", Nature, 345:60-63 (1990).
Tyson, et al., "Community Structure and Metabolism through Reconstruction of Microbial Genomes from the Environment", Nature, 428:37-43 (2004).
Venter, et al., "Environmental Genome Shotgun Sequencing of the Sargasso Sea", Science, 304:66-74 (2004).
Wang, et al., "Viral Discovery and Sequence Recovery Using DNA Microarrays", PLoS Biol., vol. 1(2):257-260 (2003).
Young, "Major Microbial Diversity Initiative Recommended", ASM News, 63(8):417-421 (1997).
International Search Report and Written Opinion, International Patent Application No. PCT/US07/08127, Aug. 5, 2008, 8 pages.
Bollmann, A. et al., "Incubation of Environmental Samples in a Diffusion Chamber Increases the Diversity of Recovered Isolates," Appl. Environ. Microbiol., vol. 73(20): 6386-6390 (Oct. 2007).
Kaeberlein, T. et al., "Isolating "Uncultivable" Microorganisms in Pure Culture in a Simulated Natural Environment," Science, vol. 296(5570): 1127-1129 (2002).
European Search report issued for EP07754624.0, dated Apr. 23, 2010 (1 page).
Office Action dated Apr. 11, 2011, received in corresponding Russian Appln. No. 2008143364/13(056447) (6 Pages).

* cited by examiner

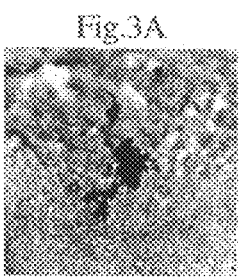 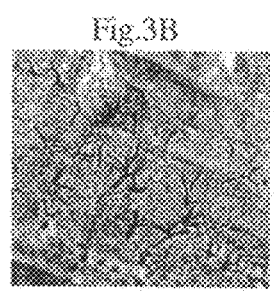 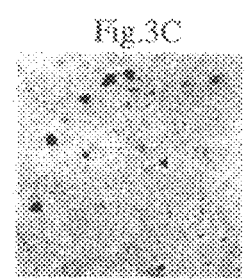
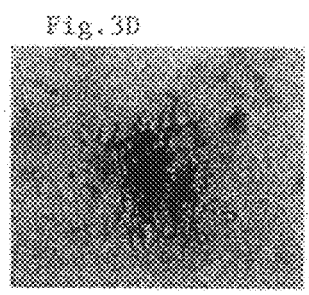 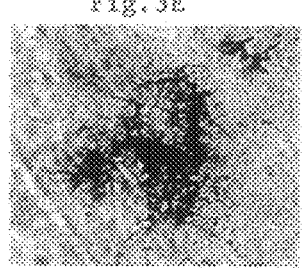

DEVICES AND METHODS FOR THE SELECTIVE ISOLATION OF MICROORGANISMS

CROSS-REFERENCE TO RELATED APPLICATIONS

This application claims the benefit of U.S. Provisional Appl. No. 60/789,101 filed Apr. 4, 2006, entitled, "Devices And Methods for the Isolation And Cultivation of Microorganisms," the contents of which are incorporated by reference in their entirety.

STATEMENT REGARDING FEDERALLY SPONSORED RESEARCH OR DEVELOPMENT

Part of the work leading to this invention was carried out with United States Government support provided under a grant from The National Institutes of Health, Grant No. R21 AI059489-01. Therefore, the U.S. Government has certain rights in this invention.

TECHNICAL FIELD

The field relates to microbiology. More specifically, the field relates to devices and methods for the isolation and/or cultivation of known and novel microorganisms.

BACKGROUND

The GenBank® sequence database, which is an annotated collection of all publicly-available nucleotide and amino acid sequences, contains sequences from approximately 30,000 species of bacteria. While this number may appear impressive, it is instructive to note that a recent estimate suggests that the sea may support as many as 2 million different species of bacteria, and a ton of soil more than double that number (Curtis et al., *Proc. Natl. Acad. Sci. USA* 99:10494-10499, 2002). Furthermore, only about 13,000 of the bacteria represented in GenBank® have been formally described, and almost all of these lie within 4 of the 40 bacterial divisions (DeLong, *Curr. Opin. Microbiol.* 4:290-295, 2001). The paucity of knowledge regarding other microbial species is similar or greater. This is at least in part due to the fact that the vast majority of microorganisms from the environment resist cultivation in the laboratory. These so called "uncultivables" represent 99-99.99% of all microbial species in nature (see, e.g., Young, *ASM News* 63:417-421, 1997).

Microbial diversity is typically examined by amplifying 16S rRNA genes from DNA samples isolated from a specific habitat. The sequences are then compared to each other and to the 16S rRNA sequences from known species. If no close match to an existing 16S rRNA gene sequence is found, then the test sequence is thought to represent a new microorganism and is termed an "uncultured microorganism." 16S rRNA genes, which are critical for translation, are the genes of choice for these experiments because they are thought to be conserved across vast taxonomic distance, yet show some sequence variation between closely related species. Phylogenetic analyses of 16S rRNA sequences obtained from direct sampling of environments suggest that uncultured microorganisms can be found in nearly every taxon within Bacteria and Archaea, and several groups at the division level have been identified with no known cultivable representatives (see, e.g., Giovannoni et al., *Nature* 345: 60-63, 1990; and Dojka et al., *Appl. Environ. Microbiol.* 66:1617-1621, 2000).

The principal reason for this disparity is that few microorganisms from environmental samples grow on nutrient media in Petri dishes. The discrepancy between the microbial total count and plate count is several orders of magnitude. Attempts to improve the recovery of microorganisms from environmental samples by manipulating growth media have been of limited success. Accordingly, new methods for isolating and growing previously uncultivable microorganisms are desirable. These methods may be useful in identifying microorganisms that are a valuable resource of novel metabolic products useful for pharmaceutical and industrial processes. In addition, these methods may be useful in identifying microorganisms critical for decomposing and recycling nutrients at a global scale.

SUMMARY

This application relates to novel devices and methods for isolating and/or culturing microorganisms.

In one aspect, a device for isolating and/or cultivating a microorganism is provided that comprises a first semi-permeable membrane defining a hollow space within. The microorganism can be a previously cultured, a previously uncultivable, or a novel microorganism. In some embodiments, the microorganism is selected from the group consisting of a bacterium, a fungus, a protist, and a microalga. In specific embodiments, the microorganism is an actinomycetes or a microfungus. In some embodiments, the microorganism is a filamentous microorganism. In specific embodiments, the microorganism is a filamentous actinobacterium, or a filamentous fungus. In certain other embodiments, the microorganism is an extremophile.

In some embodiments, the first semi-permeable membrane is folded onto itself and attached at its peripheries so as to form a hollow space within the folded membrane. In other embodiments, the first semi-permeable membrane is attached at its peripheries as well as internally creating separate chambers within the device. The first semi-permeable membrane can be made of a natural or synthetic polymer. In some embodiments, the first semi-permeable membrane is selected from the group consisting of a polycarbonate, a cellulose, an aluminum oxide, a polysulfone, an alginate, an epoxy resin, a polyacrylamide, a silica gel, and combinations thereof. The first semi-permeable membrane is attached to itself, via any method known to one of skill in the art. In specific embodiments, attachment is achieved by gluing. In some embodiments, the semi-permeable membrane has a pore size of about 0.2 μm to about 10.0 μm.

In another embodiment, the device for isolating and/or cultivating a microorganism further comprises a surface. In some embodiments, the surface is one half of a petri dish, a tissue culture dish, or any other container that has a substantially hollow interior. In other embodiments, the surface is any structure that provides a site for attachment of the semi-permeable membrane such that when the membrane is attached to the structure there is a substantially hollow space between the membrane and the structure.

In some embodiments, the device further comprises a medium for growing the microorganism. In some embodiments, the medium is provided on the inner surface of the first membrane that is in contact with the environment from which the microorganism is to be isolated and/or cultivated. The growth medium can be any medium that supports the growth of the microorganisms. In some embodiments, the medium is selected from the group consisting of agar, agarose, alginate, gelan gum, silica gels, carrageenans, gum Arabic, guar gum, traganth gum, xanthan gum, propyleneglycoalginate, microcrystalline cellulose, and combinations thereof. In certain embodiments, the medium can contain additives. In specific embodiments, the medium comprises about 0.5% to about 2.5% agar, about 1% vitamin solution and about 1% trace mineral solutions (ATCC®). In other specific embodiments, the medium comprises about 0.5% to about 2.5% gellan gum, about 1% vitamin solution and about 1% trace mineral solutions (ATCC®).

In another embodiment, the device for isolating and/or cultivating a microorganism comprises a gelating agent coated with the first semi-permeable membrane, the first semi-permeable membrane being permeable to entry of the microorganism. In some embodiments, the gelating agent is selected from the group consisting of agar, alginate, carrageenans, gum Arabic, guar gum, traganth gum, xanthan gum, propyleneglycoalginate, microcrystalline cellulose, and combinations thereof. In some embodiments, the semi-permeable membrane has a pore size of about 0.2 µm to about 10.0 µm. The semi-permeable membrane is made of any natural, synthetic, or semi-synthetic polymers. In some embodiments, the natural, synthetic or semi-synthetic polymers are selected from the group consisting of a polysulfone, an alginate, an epoxy resin, a polyacrylamide, a silica gel, and combinations thereof.

In still another embodiment, the device for isolating and/or cultivating a microorganism comprises a second semi-permeable membrane having a pore size of about 0.00001 µm to about 10.0 µm. In another embodiment, the first and second membranes have a pore size of about 0.2 µm to about 10.0 µm. In further embodiments, the first membrane has a pore size of about 0.00001 µm to about 0.2 µm, and the second membrane has a pore size of about 0.2 µm to about 10.0 µm. In certain embodiments, the first and second membranes are made of the same material. In certain other embodiments, the first and second membranes are made of different materials. In some embodiments, the first and second membranes are attached to each other at their peripheries and define a hollow space between the two membranes. In other embodiments, the semi-permeable membranes are attached at their peripheries as well as internally creating separate chambers within the device. The first and second semi-permeable membranes can be attached by any method known to one of skill in the art. In specific embodiments, attachment is achieved by gluing. In some embodiments, the device further comprises a medium for growing the microorganism. In certain embodiments the medium is provided on the inner surface of the membrane having the larger pore size, and which is in contact with the environment from which the microorganism is to be isolated and/or cultivated. The growth medium can be any medium that supports the growth of the microorganisms. In some embodiments, the medium is selected from the group consisting of agar, agarose, alginate, gelan gum, silica gels, carrageenans, gum Arabic, guar gum, traganth gum, xanthan gum, propyleneglycoalginate, microcrystalline cellulose, and combinations thereof. In certain embodiments, the medium can contain additives. In specific embodiments, the medium comprises about 0.5% to about 2.5% agar, about 1% vitamin solution and about 1% trace mineral solutions (ATCC®). In other specific embodiments, the medium comprises about 0.5% to about 2.5% gellan gum, about 1% vitamin solution and about 1% trace mineral solutions (ATCC®).

In yet another embodiment, the device comprises two semi-permeable membranes and a structure to which the two membranes can be attached. In certain embodiments, the structure is a hollow disk or ring. In some embodiments, the membranes are attached to the upper and lower surfaces of the structure. In certain embodiments, the membranes are glued to the upper and lower edges of the structure to create a substantially hollow closed space between the two membranes. In one embodiment, the first and second membranes have a pore size of about 0.00001 µm to about 10.0 µm. In another embodiment, the first and second membranes have a pore size of about 0.2 µm to about 10.0 µm. In further embodiments, the first membrane has a pore size of about 0.00001 µm to about 0.2 µm, and the second membrane has a pore size of about 0.2 µm to about 10.0 µm. In some embodiments, the first and second membranes are made of the same material. In other embodiments, the first and second membranes are made of different materials. In some embodiments, the device further comprises a medium for growing the microorganism. In other embodiments, the medium is provided on the inner surface of the membrane having the larger pore size, and which is in contact with the environment from which the microorganism is to be isolated and/or cultivated.

In some embodiments, the device further comprises modifications that allow it to be employed in the environment of interest.

In another aspect, a device for cultivating or isolating a microorganism is provided, which comprises a chamber having a solid, impermeable, outer boundary defining a substantially hollow space within. The chamber has an upper surface and a lower surface. The device further comprises a first semi-permeable membrane attached to the upper surface of the chamber and a second semi-permeable membrane attached to the lower surface of the chamber. The first and second semi-permeable membranes are attached to the chamber, via any method known to one of skill in the art. In specific embodiments, attachment is achieved by gluing.

The semi-permeable membrane can be made of a natural, synthetic, or semi-synthetic polymer. In some embodiments, the semi-permeable membrane is selected from the group consisting of a polycarbonate, a cellulose, an aluminum oxide, a polysulfone, an alginate, an epoxy resin, a polyacrylamide, a silica gel, and combinations thereof. In some embodiments, the second membrane has a pore size larger than the pore size of the first semi-permeable membrane. In other embodiments, the second membrane has the same pore size as the first semi-permeable membrane. In some embodiments, the first and second membranes have a pore size of about 0.00001 µm to about 10.0 µm. In another embodiment, the first and second membranes have a pore size of about 0.2 µm to about 10.0 µm. In further embodiments, the first membrane has a pore size of about 0.00001 µm to about 0.2 µm, and the second membrane has a pore size of about 0.2 µm to about 10.0 µm.

The microorganism can be a previously cultured, a previously unculturable, or a novel microorganism. In some embodiments, the microorganism is selected from the group consisting of a bacterium, a fungus, a protist, and a microalga. In specific embodiments, the microorganism is an actinomycetes or a microfungus. In some embodiments, the microorganism is a filamentous microorganism. In specific embodiments, the microorganism is a filamentous actinobacterium, or a filamentous fungus. In certain other embodiments, the microorganism is an extremophile.

In some embodiments, the chamber is a washer. In specific embodiments, the washer comprises a material selected from the group consisting of metal, plastic, brass, fiber, glass, ceramic, nylon, Teflon®, and combinations thereof. In some embodiments, the washer is selected from the group consisting of an inner race spacer, an outer race spacer, a fender washer, a metric washer, and a flat washer. In some embodiments, the device further comprises a medium for growing the microorganism. In other embodiments, the medium is provided on the inner surface of the membrane having the larger pore size, and which is in contact with the environment from which the microorganism is to be isolated and/or cultivated. In some embodiments, the device further comprises one or more modifications that allow it to be employed in the environment of interest.

In another aspect, a device for cultivating or isolating a microorganism is provided that comprises a washer having an upper surface and a lower surface, the washer defining a substantially hollow space within. The microorganism can be a previously cultured, a previously unculturable, or a novel microorganism. In some embodiments, the microorganism is selected from the group consisting of a bacterium, a fungus, a protist, and a microalga. In specific embodiments, the microorganism is an actinomycetes or a microfungus. In some embodiments, the microorganism is a filamentous microorganism. In specific embodiments, the microorganism is a filamentous actinobacterium, or a filamentous fungus. In certain other embodiments, the microorganism is an extremophile.

In some embodiments, the washer comprises a material selected from the group consisting of metal, plastic, brass, fiber, glass, ceramic, nylon, Teflon®, and combinations thereof. In some embodiments, the washer is selected from the group consisting of an inner race spacer, an outer race spacer, a fender washer, a metric washer, and a flat washer. In some embodiments, a first semi-permeable membrane having a pore size of about 0.00001 µm to about 0.2 µm is attached to the upper flat surface of the washer. In some embodiments, a first semi-permeable membrane having a pore size of about 0.02 µm to about 0.03 µm is attached to the upper surface of the washer. In other embodiments, a second semi-permeable membrane having a pore size of about 0.2 µm to about 10.0 µm is attached to the lower surface of the washer. In certain embodiments, a second semi-permeable membrane having a pore size of about 0.2 µm to about 0.45 µm is attached to the lower flat surface of the washer. The semi-permeable membranes can be attached to the washer, via any method known to one of skill in the art. In specific embodiments, attachment is achieved by gluing.

In some embodiments, the device further comprises a medium for growing the microorganism. In certain embodiments, the medium is provided on the inner surface of the membrane having the larger pore size, and which is in contact with the environment from which the microorganism is to be isolated and/or cultivated. In certain embodiments, the device further comprises one or more modifications that allow it to be employed in the environment of interest.

In a different aspect, a method for isolating and/or cultivating a microorganism from an environment is provided. The method comprises placing any of the devices described above in an environment of interest. The environment contains, or may contain, the microorganism. The microorganism can be a previously cultured, a previously unculturable, or a novel microorganism. In some embodiments, the microorganism is selected from the group consisting of a bacterium, a fungus, a protist, and a microalga. In specific embodiments, the microorganism is an actinomycetes or a microfungus. In some embodiments, the microorganism is a filamentous microorganism. In specific embodiments, the microorganism is a filamentous actinobacterium, or a filamentous fungus. In certain other embodiments, the microorganism is an extremophile. In certain other embodiments, the microorganism is a plankton.

The method involves allowing the microorganism to enter the device through one or more pores in the semi-permeable membrane, and form colonies within the device. The device is generally placed on the surface of, or immersed within, the environment of interest.

In certain embodiments, the environment is a natural environment, or an artificial environment. In other embodiments, the environment is a replicated version of the natural environment. In certain embodiments, the environment is selected from the group consisting of terrestrial, aquatic, space, and extreme environments. In specific embodiments, the environment is a marine environment, a fresh water environment, a wetland environment, a forest, a landfill, a mine, or a farmland. In certain other embodiments, the device is placed on the surface of, or within, sediments or soils. In other embodiments, the device is suspended in a water column. In specific embodiments, the sediment or soil is from a forest, a farmland, a tundra region, an alpine region, a landfill, a mine, a coral sediment, a siliceous sediment, a carbonate sediment, or a plant material-rich sediment.

In some cases, the microorganism may form colonies on the inner surface of the membrane in contact with the environment. In other cases, the microorganism may form colonies on or within a medium in the device. In certain other cases, the microorganism may form colonies on the outside surface of the membranes.

In certain embodiments, the method further includes opening the device, picking colonies of the microorganism and/or reinoculating the microorganism in a fresh device. In certain embodiments, the method further includes opening the device, and replica plating the inner surface of the membrane of the device that was in contact with the environment onto a nutrient-containing medium.

In certain embodiments, the method further includes identifying the microorganisms in the device. In some embodiments, identification is achieved by a method selected from the group consisting of 16S rRNA sequencing, whole genome shot gun sequencing, microarrays, and combinations thereof.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 3A is a photographic representation of actinobacterial aerial and substrate mycelia on the surface of the gellan gum base of the device of FIG. 1A with a 0.2 µm pore size bottom membrane, after 14 days of incubation of the device.

FIG. 3B is a photographic representation of actinobacterial aerial and substrate mycelia on the surface of the gellan gum base of the device of FIG. 1A with a 0.2 µm pore size bottom membrane, after 14 days of incubation of the device.

FIG. 3C is a photographic representation of actinobacterial substrate mycelia on the surface of the gellan gum base of the device of FIG. 1A with a 0.2 µm pore size bottom membrane, after 14 days of incubation of the device.

FIG. 3D is a photographic representation of actinobacterial aerial and substrate mycelia on the surface of the gellan gum base of the device of FIG. 1A with a 0.2 µm pore size bottom membrane, after 14 days of incubation of the device.

FIG. 3E is a photographic representation of actinobacterial aerial and substrate mycelia on the surface of the gellan gum base of the device of FIG. 1A with a 0.2 µM pore size bottom membrane, after 14 days of incubation of the device.

DETAILED DESCRIPTION

Figure 1A:
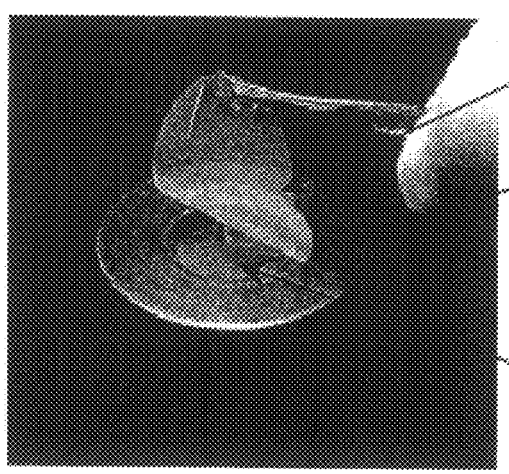
FIG. 1A is a photographic representation of a non-limiting embodiment of a device described in this application that is used to isolate and/or cultivate microorganisms. The device is comprised of a metal or plastic washer (1); a 0.03 µm pore-size polycarbonate membrane filter attached to the upper surface of the washer (2); a 0.2 µm to 0.8 µm pore-size polycarbonate membrane filter attached to the bottom surface of the washer (3); and a growth medium (e.g., agar or gellan gum base) in the space defined between the two membranes (4).

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

This application features devices and methods for isolating and cultivating microorganisms. These devices and methods are based on the discovery that microorganisms can be isolated and cultivated from an environment of interest using a device having a semi-permeable membrane into which microorganisms can enter from the environment. When the device is placed in a specific environment, microorganisms can enter the device from the environment through the pores of the membrane and form colonies within the device on the inner surface of the membrane through which it entered the device, or on the surface of, or within, a growth medium within the device.

Devices for Isolating and Cultivating Microorganisms

The growth and cultivation devices of the present invention comprise, in its simplest form, a closed or sealed semi-permeable membrane. The terms "closed" or "sealed" are used herein to mean that the semi-permeable membrane separates the space enclosed by the membrane from the environment. This separation still permits entry of microorganisms or small diffusible molecules through the pores of the semi-permeable membrane.

The semi-permeable membrane may be closed by being folded onto itself and the peripheries of the folded membrane can be attached together to create a closed inner space. The semi-permeable membrane can also be constructed as a closed bag, a balloon, or any other structure into which the microorganism can enter and grow. The semi-permeable membranes can be attached to itself, to other semi-permeable membranes, or structures such as the edges of Petri dishes, or surfaces of washers using any method known to one of ordinary skill in the art (e.g., by gluing or heat-fusing). The mode of attachment is chosen based on the ability to adhere membranes or other surfaces, and to be able to withstand environmental conditions. Most importantly, the mode of attachment is generally non-toxic for microorganisms. In some instances, a sealant is used. SuperSilicon Type 7 (Versachem Corp.), is a very sturdy compound, which holds extremely well under most adverse conditions. Tests on this sealant's toxicity proved negative as the sealant exhibited no effect on *E. coli* growth. The semi-permeable membrane can also be attached to a surface (e.g., one half of a petri dish, or other container), to create a closed space between the surface and the membrane. The semi-permeable membrane has a pore size of about 0.2 µm to about 10.0 µm. By "about" as used throughout this disclosure, is meant a numeric value having a range of ±20% around the cited value. The semi-permeable membranes for the devices described herein can be made of any natural or synthetic polymer. The membranes are generally chosen so that they are sufficiently robust to withstand the environment in which they are placed. Non-limiting examples of membranes for use herein include polycarbonate membranes, cellulose membranes, and aluminum membranes.

In a different form, the device of the invention comprises two semi-permeable membranes. The two membranes are attached to each other at their peripheries and define a hollow space between the two membranes. The two semi-permeable membranes can also be attached to a surface such as a ring, a disk, or a solid surface. The two membranes can be made of the same or of different materials (e.g., natural or synthetic polymers). In addition, the membranes may have the same pore sizes or different pore sizes. For example, the two membranes have a pore size of about 0.2 µm to about 10.0 µm. Alternatively, one of the two membranes has a pore size of about 0.00001 µm to about 0.2 µm, and the second membrane has a pore size of about 0.2 µm to about 10.0 µm.

The devices described above can also include further modifications, such as attachments to weigh the membrane down to allow it to remain on the surface of the environment in which it is placed, or hooks or clasps to hold or position the device in a specific environment. The shape, size, and modifications of the device can easily be determined by one of ordinary skill in the art depending upon several factors including, but not limited to, the nature of the environment from which the microorganism is to be isolated, the temperature of the environment, the number of colonies to be isolated, etc.

One device of the invention comprises a structure having an upper surface and a lower surface, and having a solid, impermeable, outer boundary defining a hollow space within. Semi-permeable membranes are attached to the upper and lower surfaces of the structure, thereby enclosing the hollow space within the structure. The membranes attached to the upper and lower surfaces of the structure can be made of the same or of different materials. Useful materials for use in the invention include any natural or synthetic polymer. In addition, the membranes may have the same pore sizes or different pore sizes. In certain non-limiting examples, the two membranes have a pore size of about 0.2 µm to about 10.0 µm. In other non-limiting examples, one of the two membranes has a pore size of about 0.00001 µm to about 0.2 µm, and the second membrane has a pore size of about 0.2 µm to about 10.0 µm.

In a specific embodiment, the structure comprises a washer. A washer is a thin disk with a hole, usually in the middle, and it is normally used to support the load of a threaded fastener. Any kind of washer can be used in the devices of the invention. Non-limiting examples of washers include, a metal washer, a plastic washer, a brass washer, a fiber washer, a metric washer, a nylon washer, a Teflon® washer, an inner race spacer, an outer race spacer, a fender washer, and a flat washer. The semi-permeable membranes, as described above, are attached to the upper and lower surfaces of the washer, thereby enclosing the hollow space of the washer.

All of the devices of the invention described above can further include a growth medium. The growth medium can be any medium that supports microbial growth. Non-limiting examples of suitable media include agar base, agarose, gelan gum, alginate, propylenglycoalginate, hydrogels, silica gels, carrageenans, gum Arabic, guar gum, traganth gum, xanthan gum, microcrystalline cellulose, and combinations thereof. The media can also contain additives such as vitamins and minerals. Specific non-limiting examples of growth media include Base 1 (about 0.5% to about 2.5% agar, 1% vitamin solutions, and 1% trace mineral solutions), or Base 2 (about 0.5% to about 2.5% gellan gum, 1% vitamin solutions, and 1% trace mineral solutions).

Some microbes may require specific surfaces such as a solid surface for attachment and growth. In the absence of such surfaces, these organisms may be unable to divide and/or form colonies. In such instances (e.g., those involving growing microorganisms from marine sandy tidal flats), sterilized sand may be added to the agar in the medium.

Certain devices for isolating and/or cultivating microorganisms can be constructed by enclosing or encapsulating a suitable growth medium with a natural or synthetic polymer which can form a semi-permeable film or coating. The polymers may have a pore size of about 0.2 µm to about 10.0 µm, but may also have a pore size of about 0.00001 µm to about 10.0 µm. Non-limiting examples of natural or synthetic polymers that can be used for the devices described herein include polysulfones, alginates, epoxy resins, polyacrylamides, silica gels, and combinations thereof.

Methods for Isolating and Cultivating Microorganisms

The devices described herein are useful in methods for isolating and/or cultivating microorganisms. Such methods generally involve providing a device of the invention in an environment from which a microorganism is to be isolated and allowing one or more microorganisms to enter the device and form colonies within the device. The device is generally placed on the surface of, or immersed in, the desired environment. Microorganisms enter the device through the pores of the semi-permeable membrane and form colonies on the inner surface of the membrane through which it enters the device. In those devices where a growth medium is present, the microorganism forms colonies on the surface of the growth medium, or within the growth medium. In some instances, the microorganisms may form colonies on the outside surface of the device. The microorganisms can then be isolated, cultivated, and identified.

Types of Microorganisms

The microorganism to be isolated and cultivated can be a known microorganism, a previously unculturable microorganism, or a novel microorganism. In some cases, the microorganism to be isolated and/or cultivated is from one of the three known domains of cellular organisms namely, Bacteria, Archaea, or Eukarya. Non-limiting examples of microorganisms that can be isolated and cultivated using the devices described herein are bacteria, fungi, protists, and microalgae. Although any microorganism can be isolated and cultivated with the devices described, the devices are most useful for filamentous microorganisms. This is because filamentous microorganisms can easily enter the device through the pores of the semi-permeable membrane. Non-limiting examples of filamentous microorganisms include filamentous actinobacteria and filamentous fungi.

Environments from which the Microorganisms are Isolated and/or Cultivated

Microorganisms can be isolated and cultivated from any environment. The environment can be a natural environment, an artificial environment, or a replicated version of the natural environment. "A replicated version of the natural environment" means any environment created in a laboratory setting to recapitulate the natural environment to the extent that this is possible. For example, a replicated version of a marine environment may be an aquarium containing water and sediment from the marine environment. A replicated version of a forest soil environment may include a container containing soil obtained from the forest. Non-limiting representative environments from which microorganisms can be obtained include terrestrial environments, aquatic environments, extreme environments, and planetary or other space environments.

Some environments include fresh water, seawater, sediments and soils, such as from a forest, a farmland, a tundra region, an alpine region, a landfill, or a mine. Marine sediments include, but are not limited to, a coral sediment, a siliceous environment, a carbonate environment, and a plant material-rich environment (e.g., mangrove). Other useful environments include specific areas in a building, e.g., a hospital, with microorganisms being isolated from a site such as the ventilation system, a bathroom wall surface, or a hospital room surface.

Other environments from which microorganisms can be isolated include extreme environments. By "extreme environment" is meant any environment wherein conditions such as pH level, air pressure, temperature, salinity, radiation, dryness (desiccation), and oxygen level are significantly different from the rest of the Earth where most organisms normally live. Such environments are expected to lead to the discovery of microorganisms including, but not limited to, anaerobes, thermophiles, psychrophiles, acidophiles, alkalophiles, halophiles, barophiles, and xerophiles.

As space exploration moves forward, the new environments that are identified will be ideal locations in which the devices described herein may be useful for identifying new microorganisms. The devices can be taken into space (e.g., Mars) and placed in these new environments, or soil or other materials brought from space can be used to identify microorganisms in a laboratory on Earth.

The devices described herein may also be used to isolate and cultivate microorganisms from a subject such as a human or a domesticated animal. The device may be placed in a location where microorganisms are expected to be present, such as the mouth. In order to be used in this manner, the device may need to be modified (e.g., addition of a structure that allows the semi-permeable membrane to be placed in/at a particular location). For example, to identify microorganisms from the mouth of a human subject, any of the devices described herein may be attached to a wooden or plastic strip to hold the device in the mouth of the subject. Accordingly, these methods can be useful in diagnosing microbial infections in a subject.

Incubation

In order to isolate and/or cultivate the microorganisms, the devices described herein are incubated in the environment of choice for a sufficient period of time to allow microorganisms to enter the device and form colonies. Typically, the devices are incubated on the surface of or immersed in the environment. For example, the device may be placed on the surface of forest soil, or a replicated version of this forest environment. Alternatively, or additionally, the device may be inserted within the soil. When the device is placed on the surface of the environment, and the device is one with at least semi-permeable membranes, the semi-permeable membrane having the larger pore size is placed in contact with the environment containing the microorganism to be isolated and cultivated.

The device may be incubated in the environment of choice for as long as the investigator has determined it to be necessary, e.g., for at least a day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days. In some cases the device is incubated in the environment of choice for about 1 day to about 14 days, from about 5 days to about 7 days, or from about 5 days to about 14 days.

If the device is incubated in a replicated version of the natural environment, incubation is typically performed at room temperature, or at the temperature the natural environment has been measured to be. However, the temperature for incubation can be determined by one of ordinary skill in the art depending on the specific situation at hand.

Methods of Detecting Microorganisms

After incubation of the devices described herein in the environment of choice for a specified period, the device can be opened to determine if colonies have formed. Detection may be by any known method known in the art including, but not limited to, simple visual inspection or by microscopic methods.

Prior work with marine microbes indicates that in sediments, solitary microorganisms are rare and that most microbes form microcolonies on the surface of sand grains and detrital particles. These microcolonies, which are quite small and consist only of a few dozen to several hundred cells, are many times smaller than can be detected under a dissecting microscope. Naturally, such colonies will be missed unless they are specifically searched for. One method of visualizing these microcolonies is under a compound microscope using vital dyes (e.g., acridine orange, fluorescein isothiocyanate, rhodamine, calcofluor, europium chelate). Nomarski Differential Interference Contrast microscopy is also very useful. However, even if the cells are contrasted against the background by vital staining/Nomarski microscopy, handling these colonies for subculturing can be challenging. Therefore, other ways to sample and manipulate milligrams of agar and handle very small numbers of cells have been developed. With semi-liquid agar as the growth medium, a tungsten wire has proven very useful, with or without a micromanipulator to operate it. Also of particular help is an additional prism in the microscope to compensate for the image inversion that is an almost universal feature of compound microscopes. With this modification, the microscope shows objects with no left-to-right inversion, which greatly facilitates manipulation of the tungsten wire. A microscope facility particularly suitable for handling such samples may include, e.g., a Zeiss Axioplan 2 MOT equipped for fluorescence imaging, a Nomarski/DIC microscope, a phase contrast microscope, and a state of the art imaging system (e.g., a Hamamatsu ultrafast high resolution cooled CCD camera operated by an Improvision software package OpenLab, which is capable of confocal imaging and 3-D rendering).

Identification of Microorganisms

To identify the microorganism(s) that grow in the devices of the invention, cells from the colonies obtained from the device can be analyzed by any method known in the art. For example, one useful identification method is 16S RNA gene sequencing. This method involves isolating DNA from the microorganism(s), for example, by using a Qiagen DNA Mini Kit (Qiagen, Valencia, Calif.). The 16S rRNA gene from the microorganism(s) can be amplified using primers for the 16S rRNA gene by PCR, and the amplified products can be sequenced, for example, by using a Big Dye terminator cycle sequencing kit (Applied BioSystems, Foster City, Calif.). A comparison of the sequenced gene using, e.g., the online GenBank® database with known 16S RNA genes can identify the organism and can show whether or not it represents a new species/genus.

Other methods of identifying the microorganisms include using microarrays (see, e.g., Wang et al., *PLoS Biol* 1:2003), or whole genome shotgun sequencing (see, e.g., Tyson et al., *Nature*, 428(6978):37-43, 2004; and Venter et al., *Science*, 304(5667):66-74, 2004).

Filamentous microorganisms, in particular, can be identified by using methods for filament identification known in the art including, but not limited to, wet mounting, Gram staining, Neisser staining, PHB staining, sheath staining, polyscaccharide (India Ink) staining, and sulfur oxidation testing.

Reinoculation

The colonies obtained from the devices of the invention can be used to reinoculate the devices described herein to increase microorganism numbers. For example, colonies of microorganisms can be picked up about 5 days to about 7 days after incubation in a given environment using sterile tooth picks or sterile Pasteur pipettes, homogenized, and used to inoculate new devices. In other cases, the microorganisms are picked up after about 10 days to about 14 days after incubation in a given environment. This amount of time will allow certain microorganisms to form aerial mycelia, making it easier to pick the microorganism for reinoculation.

The inoculated devices can be replaced in the environment from which the microorganism was obtained, or placed in a replicated version of this environment. The semi-permeable membrane(s) will allow components of the natural environment to diffuse into the chamber that are needed by the microorganism to grow.

Alternatively, the devices can be placed into a different, or artificial environment. In such cases it may be possible to select microorganisms that have different or newly obtained characteristics such as the ability to grow in salt as well as fresh water, or ability to grow at a range of temperatures rather than room temperature.

The invention is illustrated further by the following examples, which are not to be construed as limiting the invention in scope or spirit to the specific procedures described therein. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Construction of a Device for In Situ Cultivation of Microorganisms

Figure 1B:
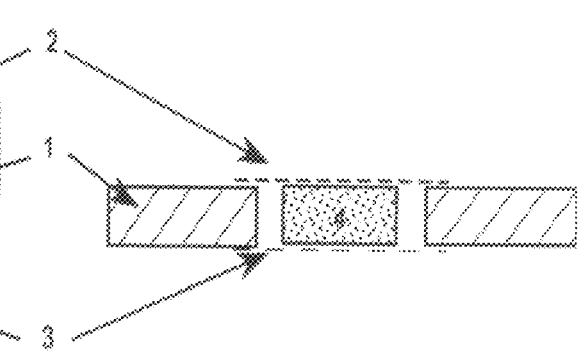
FIG. 1B is a schematic representation of a cross-sectional view of the device shown in FIG. 1A.

An exemplary device for in situ cultivation of microorganisms according to the invention is illustrated in FIGS. 1A and 1B of this application.

The device is comprised of a metal or plastic washer (e.g., 70 mm outer diameter, 33 mm inner diameter, 3 mm in thickness; Bruce Watkins Supply, Inc., Wilmington, N.C.), and two semi-permeable polycarbonate membranes having different pore sizes. One of the polycarbonate membranes had a pore size of about 0.03 µm (Osmonics, Inc., Westborough, Mass.), whereas the second membrane had a pore size of about 0.2 µm to about 0.5 µm (ISOPORE™, Millipore Corporation). Between the two polycarbonate membranes is a hollow space within which microorganisms can grow.

To construct the device, the polycarbonate membrane having the larger pore size was glued with Silicon Glue II (General Electric, Waterford, N.Y.) to the bottom surface of the washer. After this membrane had been affixed to the bottom of the washer, 3 ml of Base 1 media (1.2% agar, 1% vitamin solution, and 1% trace mineral solutions (ATCC®) or 3 ml Base 2 media (1.5% gellan gum, 1% vitamin solution, and 1% trace mineral solutions (ATCC®) was poured onto this membrane partially filling the inner space. Next, the upper surface of the washer was sealed with the polycarbonate membrane having the smaller pore size using Silicon Glue II, leaving an air space between the top of the media surface and the underside of the upper membrane. All manipulations were made under aseptic conditions.

Example 2

Collection and Cultivation of Unique Bacterial Species from a Soil Sample

To identify microorganisms present in a soil sample, a soil sample was collected from a garden in Verrill Farm (Concord, Mass., USA), and the sample was air dried and stored in a plastic container before use.

Several devices, similar to the one described in Example 1 and hereinafter referred to as "traps", were placed on the surface of the soil sample with the membrane having the larger pore size in contact with the surface of the soil. The devices were incubated on the surface of the soil at room temperature for 5 to 7 days. After incubation, the devices were examined for evidence of the presence of microorganisms.

Figure 2A:
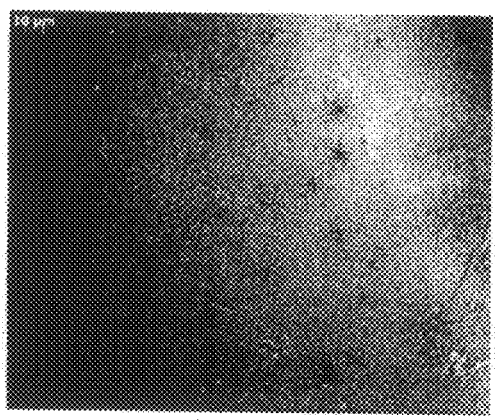
FIG. 2A is a photographic representation of actinobacterial microcolonies growing within the gellan gum base of the device described in FIG. 1A with a 0.2 µm pore size bottom membrane, after 7 days of incubation of the device at room temperature.
Figure 2B:
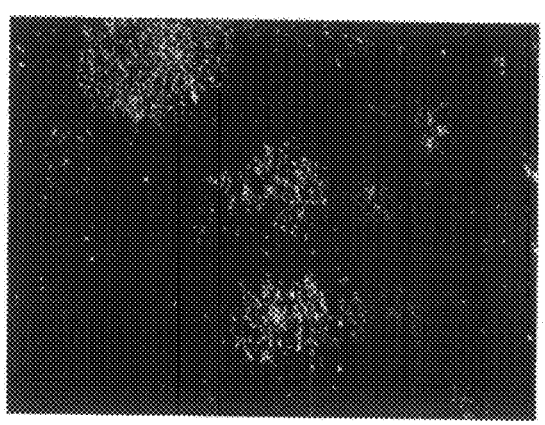
FIG. 2B is a photographic representation of an enlarged view of the actinobacterial microcolonies of FIG. 2A.

Filamentous microorganisms were able to enter through the pores of the lower membrane, and formed colonies on the growth media inside the devices after 5 to 7 days of incubation (see, FIG. 2). The upper membrane of the traps were then peeled off, the traps were overturned, the lower membrane was then peeled off, and the slab of the internal material was dropped onto a sterile Petri dish. After an additional 5 to 7 days of incubation at room temperature, many strains formed aerial mycelium (see, FIG. 3) and could be easily reinoculated.

Fifty seven actinobacterial microcolonies were randomly picked up from the surface of the gellan gum base of the device described in FIG. 1A with a 0.2 µm pore size bottom membrane (i.e., the membrane attached to the bottom surface of the washer) and reinoculated onto a nutrient medium with gellan gum as a solidifying agent.

About half of the isolates belonged to different species of *Streptomyces* (see, Table 1). The remaining isolates represent rare actinobacterial genera, most of which are well known as producers of antibiotics.

TABLE 1

List of the Actinomycetes Isolated From the Growth Media on the Bottom Membrane

| Isolates | No. of Isolates |
|---|---|
| *Actinoplanes* sp. | 6 |
| *Amycolatopsis* sp. | 1 |
| *Arthrobacter* sp. | 1 |
| *Catellatospora* sp. | 1 |
| *Cellulomonas* sp. | 2 |
| *Cellulosimicrobium* sp. | 2 |
| *Kribbella* sp. | 2 |
| *Lentzea* sp. | 4 |
| *Microbacterium* sp. | 2 |
| *Mycobacterium* sp. | 1 |
| *Nocardioides* sp. | 4 |
| *Rhodococcus* sp. | 1 |
| *Streptomyces* sp. | 30 |

There was little overlap between species isolated from the device described herein, and species from the same soil sample that grew on a Petri dish under conventional conditions (see, Table 2). This indicates the ability of the device described herein to access unique bacterial species.

TABLE 2

List of the Actinomycetes Isolated From Agar Plates (Nutrient agar, Humic acid agar, Malt extract agar)

| Isolates | No. of Isolates |
|---|---|
| *Arthrobacter* sp. | 12 |
| *Cellulomonas* sp. | 2 |
| *Micromonospora* sp. | 1 |
| *Mycobacterium* sp. | 5 |
| *Nocardia* sp. | 5 |
| *Nocardioides* sp. | 1 |
| *Nonomuraea* sp. | 5 |
| "*Parastreptomyces* sp" | 2 |
| *Rhodococcus* sp. | 1 |
| *Streptomyces* sp. | 60 |
| *Streptosporangium* sp. | 1 |
| *Terrabacter* sp. | 2 |

Example 3

Cultivation of Fungal Species from a Soil Sample

To isolate fungi from a soil sample, the device described in Example 1 was modified such that the membrane attached to the bottom surface of the washer ("bottom" membrane) was an ISOPORE™ Membrane Filter (Millipore Corporation) having a pore size greater than 0.2 µm.

Such a modified device was placed on the surface of a soil sample from Massachusetts with the ISOPORE™ membrane in contact with the surface of the soil, and incubated at room temperature for 5 days. After the incubation period, the device was opened, and sterile Pasteur pipettes were used to cut pieces of the agar or gellan gum base to isolate fungal mycelium that was then inoculated on malt extract nutrient medium.

All fungal isolates from this soil sample belonged to the phylum Ascomycota. Notably, no overlap was found between the genera from the devices described herein (see, Table 3)

and species from the same soil sample that grew on agar plates under conventional conditions (see, Table 4).

TABLE 3

Fungal Isolates From Devices

| Isolate | Closest match | Accession No. | Nucleotide Identity (%) | Pore Size of Bottom Membrane (μm) |
|---|---|---|---|---|
| MF1 | Neocosmospora vasinfecta | NVU32414 | 99 | 0.6 |
| MF2 | Fusarium oxysporum | AB110910 | 99 | 0.6 |
| MF3 | Chaetomium globosum | AB048285 | 99 | 0.8 |
| MF4 | Fusarium oxysporum | AB110910 | 99 | 0.6 |
| MF6 | Fusarium oxysporum | AB110910 | 99 | 0.8 |
| MF8 | Neocosmospora vasinfecta | NVU32414 | 99 | 0.8 |
| MF9 | Neocosmospora vasinfecta | NVU32414 | 99 | 0.8 |
| Mf10 | Fusarium oxysporum | AB110910 | 99 | 0.6 |
| E8 | Neocosmospora vasinfecta | NVU32414 | 99 | 0.4 |

TABLE 4

Fungal Strains Isolated By Direct Cultivation From A Soil Sample From Massachusetts

| Isolate | Closest Match | Accession No. | Nucleotide Identity (%) |
|---|---|---|---|
| Pd1 | Eupenicillium javanicum | EJU21298 | 99 |
| Pd2 | Eupenicillium javanicum | EJU21298 | 98 |
| Pd3 | Eupenicillium javanicum | EJU21298 | 99 |
| Pd4 | Eupenicillium javanicum | EJU21299 | 99 |
| Pd5 | Eupenicillium javanicum | EJU21300 | 99 |
| Pd7 | Penicillium purpurogenum | AF245268 | 99 |
| Pd8 | Penicillium purpurogenum | AF245268 | 99 |
| Pd9 | Metarhizium anisopliae | AB250412 | 99 |

These findings suggest that the devices described herein can be used to isolate novel fungi, or other novel microorganisms.

Example 4

Empty Traps

"Empty Traps" are devices similar to those described in Example 1, except lacking a specific growth medium.

Figure 4:
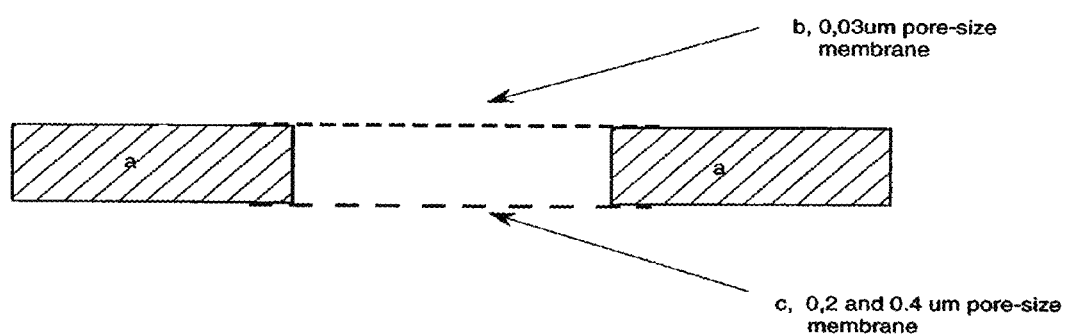
FIG. 4 is a schematic representation of a cross-sectional view of another non-limiting embodiment of a device of the invention used for isolating and cultivating microorganisms. The device shown in the figure is formed by a metal or plastic washer (a); a 0.03 µm pore-size polycarbonate membrane filter attached to the upper surface of the washer (b); and a 0.2 µm or 0.4 µm pore size polycarbonate membrane filter attached to the bottom surface of the washer (c).

An exemplary empty trap device is schematically represented in FIG. 4. Such a device comprises a metal or plastic washer (a) and two semi-permeable membranes (b and c), wherein the membranes are attached to the upper and lower surfaces of the washer. In some cases, both semi-permeable membranes of the empty trap have the same pore size (e.g., about 0.2 μm to about 10.0 μm). In other cases, the membrane attached to the upper surface of the washer has a pore size that is smaller (e.g., about 0.00001 μm to about 0.2 μm) than the pore size of the membrane attached to the lower surface of the washer (e.g., about 0.2 μm to about 10.0 μm).

Example 5

Growth of Microorganisms Using an Empty Trap Device

Figure 5A:
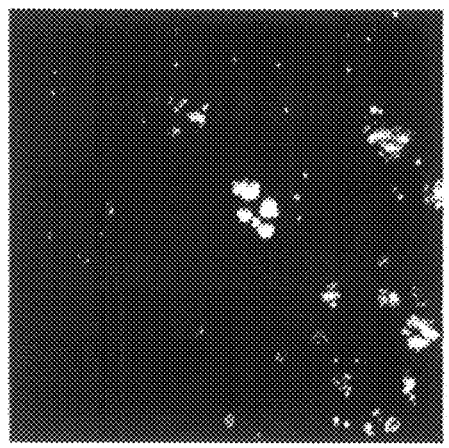
FIG. 5A is a photographic representation of colonies of bacteria growing on the 0.4 µm pore size membrane attached to the bottom surface of the washer of FIG. 4.
Figure 5B:
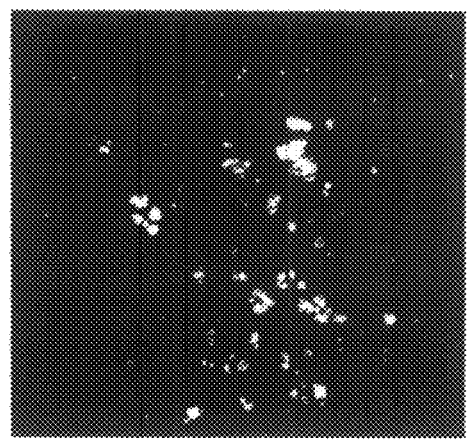
FIG. 5B is a photographic representation of colonies of bacteria growing on the 0.4 µm pore size membrane attached to the bottom surface of the washer of FIG. 4.

Four empty trap devices were inserted into a soil sample obtained from Massachusetts and incubated for 5 days at room temperature. Then, the traps were opened, and examined with a DIC stereomicroscope. As shown in FIG. 5, empty traps were found to be capable of serving as growth chambers for microorganisms. The microorganisms formed colonies on the inner surface of the membrane, belonging primarily to actinomycetes. Fungal mycelia were also present.

Figure 6:
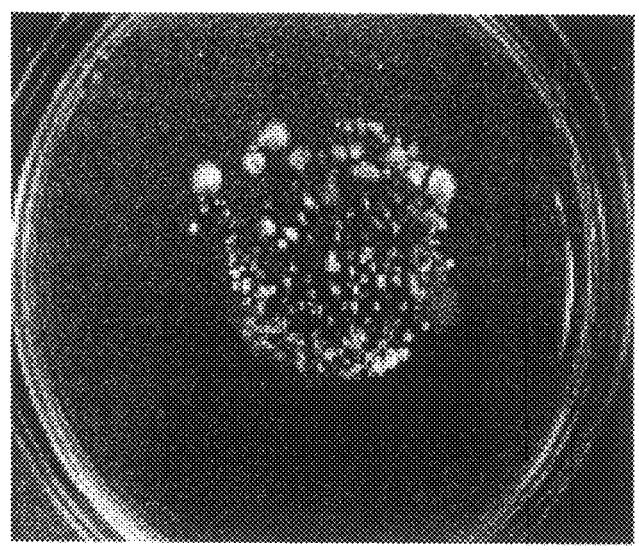
FIG. 6 is a photographic representation of colonies that form on nutrient agar 7 days after replica-plating a 0.4 µm pore size membrane attached to the bottom surface of the washer of FIG. 4.

The colonies on the inner surface of the membrane attached to the lower surface of the washer were transferred to agar plates using a replica plater and incubated at room temperature, for another 7 days (see, FIG. 6).

These experiments indicate that empty traps are useful devices for isolating and cultivating microorganisms.

Example 6

Construction and Use of a Gelating Agent Device for Isolation of Microorganisms

A natural, semi-synthetic, or synthetic gelating agent including, but not limited to, agar, alginate, carrageenans, gum Arabic, guar gum, traganth gum, xanthan gum, propyleneglycoalginate, and microcrystalline cellulose, is used as the matrix for this device.

To construct the gelating agent spheres, the gelating agent, for example, agar (about 0.7% to about 2%), is autoclaved and then cooled to 40° C. to 50° C. The agar is then made into a sphere by dripping agar droplets through a nozzle into cold mineral oil. The agar's sphere size is adjusted by the nozzle diameter and dripping rate. Typically, the diameter of the agar sphere is about 0.01 mm to about 5 mm (usually 2-3 mm).

The gelating agent spheres are then coated with a natural or synthetic polymer. For coating the sphere, the dried gelating agent spheres are introduced into the polymer solution of choice, and are then transferred into a medium that enables coating of the spheres with several layers of the polymer, thereby forming the desired gelating agent devices for isolation of microorganisms. For example, the dried agar spheres are immersed in a solution of 10% polysulfone (Sigma-Aldrich, Product No. 42, 830-2) in dimethylformamide and transferred to water in order to obtain the desired polymeric coating.

To obtain microorganisms from a desired environment, the gelating agent device is placed in the environment of choice (e.g., on the surface of, or within, soil from a forest; or on the surface of, or within, marine sediment), for a period determined by the investigator as effective for microorganisms to enter the device and form colonies.

After the period of incubation, the device is cut and the agar is examined visually or microscopically for colonies of microorganisms. The microorganisms are isolated and, if desired, reinoculated into new devices.

Example 7

Use of Device for Isolation of Microorganisms

To identify microorganisms present in a soil sample the trap described in Example 1 was employed as described in Example 2 using various different soil samples collected in the United States.

Table 5 below summarizes the organisms that were isolated from the trap.

TABLE 5

Microorganisms Isolated from the Trap

| Isolate | % Homology | Closest Related Genus | Bioactivity |
|---|---|---|---|
| B0579 | 86.3 | Niastella | active |
| B1275 | 93.1 | Lechevalieria | active |
| B1146 | 94.2 | Actinoplanes | active |
| B0856 | 96.1 | Streptacidiphilus | active |
| B0919 | 97.2 | Couchioplanes | active |
| B1113 | 97.3 | Actinocorallia | active |
| B0654 | 97.3 | Amycolatopsis | active |
| B1023 | 97.3 | Streptomyces | active |
| B0733 | 98.0 | Pseudonocardia | active |
| B0577 | 98.2 | Kribbella | active |
| B1155 | 98.2 | Nocardia | active |
| B0905 | 98.3 | Kitasatospora | active |
| B1150 | 98.3 | Kribbella | active |
| B0492 | 98.3 | Nocardia | active |
| B0822 | 98.6 | Catenulispora | active |
| K0033 | 98.6 | Saccharothrix | active |
| B0494 | 98.7 | Kribbella | active |
| B0498 | 98.7 | Rhodococcus | active |
| B1044 | 99.0 | Catenulispora | active |
| B1114 | 99.1 | Catenulispora | active |
| B0536 | 99.9 | Kocuria | active |
| KG-E4 | 100.0 | Catellatospora | active |
| KG-MS5 | 100.0 | Lentzea | active |
| KG-MS17 | 100.0 | Nocardioides | active |
| B0775 | 100.0 | Oerskovia | active |
| B0950 | 93.3 | methylobacillus | not active |
| P1252 | 95.0 | Rhodococcus | not active |
| B1262 | 95.6 | Micromonospora | not active |
| B1226 | 96.0 | Microbacterium | not active |
| B0735 | 96.2 | Kitasatospora | not active |
| B0587 | 96.6 | Cellulosimicrobium | not active |
| B0891 | 96.6 | Micromonospora | not active |
| B0776 | 96.6 | Streptomyces | not active |
| B0893 | 96.9 | Actinoplanes | not active |
| B0820 | 97.0 | Nocardia | not active |
| B1105 | 98.0 | Kribbella | not active |
| B0548 | 99.0 | Promicromonospora | not active |
| B0599 | 99.3 | Lechevalieria | not active |
| KG-F4 | 100.0 | Nocardioides | not active |
| B1253 | 93.0 | Lechevalieria | not tested |
| B1142 | 94.8 | Catenulispora | not tested |
| B1003 | 95.4 | Catenulispora | not tested |
| B1030 | 96.4 | Actinostreptospora | not tested |
| B1338 | 96.7 | Actinoplanes | not tested |
| B1267 | 97.2 | Actinoplanes | not tested |
| B0851 | 97.6 | Agromyces | not tested |
| B0861 | 98.9 | Oerskovia | not tested |
| B0663 | 99.7 | Arthrobacter | not tested |
| B0768 | 99.9 | Nocardioides | not tested |
| B1144 | 99.9 | Streptosporangium | not tested |

% homology refers to how similar the 16s rDNA from the isolated organism is to any known strain the Genbank ® database.
Bioactivity was measured using a spot on lawn assay with activity against either *Bacillus, E. coli,* or *H. influenza.*

Bioactivity was measured using a spot on lawn assay with activity against either *Bacillus, E. coli,* or *H. influenza.*

The invention claimed is:

1. A device for trapping, isolating, and culturing a filamentous microorganism from a natural environment, consisting of:
   a first semi-permeable membrane having a pore size of about 0.00001 to less than 10.0 μm;
   a second semipermeable membrane having a pore size of 0.2 μm to 10.0 μm; and
   a medium that permits the growth of microorganisms,
   the first semipermeable membrane having a pore size smaller than the second semipermeable membrane,
   the first and second semipermeable membranes being attached to each other at their peripheries and defining a sealed hollow space between the two membranes, and the medium being provided in the sealed space between the two membranes,
   the device being configured to allow the microorganism in the natural environment to enter the closed, sealed space through pores in the first and/or second membranes and be trapped therein.

2. The device of claim 1, wherein the medium comprises a gelating agent.

3. The device of claim 1, wherein the first and second semi-permeable membranes each comprise a material selected from the group consisting of, an aluminum oxide, a polysulfone, an alginate, an epoxy resin, a polyacrylamide, a silica gel, and combinations thereof.

4. The device of claim 1, wherein the first and second membranes are comprised of the same material.

5. The device of claim 1, wherein the first and second membranes are comprised of different materials.

6. The device of claim 1, wherein the medium comprises agar, alginate, carrageenans, gum Arabic, guar gum, traganth gum, xanthan gum, propyleneglycolalginate, microcrystalline cellulose, or a combination thereof.

7. A device for trapping, isolating, and culturing a filamentous microorganism from a natural environment, consisting of:
   (a) a structure having a solid, impermeable, outer boundary defining a closed, sealed, hollow, inner space within the structure having an upper surface and a lower surface;
   (b) a medium that permits growth of the microorganism contained within the inner space;
   (c) a first semi-permeable membrane having a pore size of about 0.00001 μm to less than 10.0 μm and being attached to the upper surface of the structure; and
   (d) a second semi-permeable membrane having a pore size of about 0.2 μm to about 10.0 μm and being attached to the lower surface of the structure, the second semipermeable membrane having a pore size larger than the pore size of the first semi-permeable membrane,
   the first and second semipermeable membranes comprising an aluminum oxide, a polysulfone, an alginate, an epoxy resin, a polyacrylamide, a silica gel, or combinations thereof,
   the device being configured to allow the microorganism to enter its closed, sealed space through the pores in the first and/or second semi-permeable membrane.

8. The device of claim 7, wherein the structure is a washer comprising upper and lower flat surfaces to which the first and second semi-permeable membranes are attached and which defines the closed, sealed, hollow, inner space.

9. The device of claim 8, wherein the washer comprises a material selected from the group consisting of metal, plastic, brass, fiber, glass, ceramic, nylon, polytetrafluoroethylene, and combinations thereof.

10. The device of claim 7, wherein the first and second membranes are comprised of the same material.

11. The device of claim 7, wherein the medium comprises agar, alginate, carrageenans, gum Arabic, guar gum, traganth gum, xanthan gum, propyleneglycolalginate, microcrystalline cellulose, or a combination thereof.

12. The device of claim 7, wherein the first and second membranes are comprised of different materials.

13. The device of claim 7, wherein the first semipermeable membrane has a pore size of about 0.00001 μm to 0.2 μm, and the second semipermeable membrane has a pore size of about 0.2 μm to 0.45 μm.

14. The device of claim 13, wherein the first semipermeable membrane has a pore size of about 0.03 μm, and the second semipermeable membrane has a pore size of about 0.2 μm to 0.45 μm.

15. A method for trapping, isolating, and culturing a microorganism from a natural environment, comprising:
 (a) placing the device of claim 7, in the natural environment containing the microorganism; and
 (b) allowing the microorganism to enter the closed, sealed space through a pore in the first and/or second semi-permeable membrane of the device and to form colonies therein.

16. The method of claim 15, wherein the first and/or second semi-permeable membrane of the device is placed in contact with the environment, or is immersed within the environment.

17. The method of claim 15, wherein the microorganism entering the device through the pore is a bacterium, a fungus, a protist, or a microalga.

18. The method of claim 17, wherein the microorganism is a filamentous microorganism.

19. The method of claim 18, wherein the filamentous microorganism is a filamentous actinobacterium, a filamentous fungus, or combinations thereof.

20. A method for isolating a microorganism from a natural environment and culturing the microorganism, comprising:
 (a) placing the device of claim 1, in the natural environment which contains the microorganism; and
 (b) allowing the microorganism to enter the sealed, closed space of the device through a pore in the first and/or second semi-permeable membrane and to form colonies therein.

\* \* \* \* \*

UNITED STATES PATENT AND TRADEMARK OFFICE
CERTIFICATE OF CORRECTION

Page 1 of 1

PATENT NO. : 9,249,382 B2
APPLICATION NO. : 11/732346
DATED : February 2, 2016
INVENTOR(S) : Ekaterina Gavrish, Kim Lewis and Slava S. Epstein It is certified that error appears in the above-identified patent and that said Letters Patent is hereby corrected as shown below:

In the Specification

Column 1, Line 18 delete "Part of the work leading to this invention was carried out with United States Government support provided under a grant from The National Institutes of Health, Grant No. R21 AI059489-01. Therefore, the U.S. Government has certain rights in this invention." and insert the following:
--This invention was made with government support under Grant Number AI059489 awarded by the National Institutes of Health. The United States government has certain rights in the invention.--

Signed and Sealed this
Eighth Day of December, 2020

Andrei Iancu
*Director of the United States Patent and Trademark Office*